(12) United States Patent
McCreery et al.

(10) Patent No.: US 12,329,870 B2
(45) Date of Patent: Jun. 17, 2025

(54) MOBILE SYSTEMS FOR MICROWAVE ASSISTED SURFACE DECONTAMINATION AND DECONTAMINATION METHODS

(71) Applicant: Zeteo Tech, Inc., Sykesville, MD (US)

(72) Inventors: Thomas McCreery, Sykesville, MD (US); Wayne A. Bryden, Sykesville, MD (US); Emily Caton, Sykesville, MD (US)

(73) Assignee: Zeteo Tech, Inc., Sykesville, MD (US)

( * ) Notice: Subject to any disclaimer, the term of this patent is extended or adjusted under 35 U.S.C. 154(b) by 0 days.

(21) Appl. No.: 18/529,901

(22) Filed: Dec. 5, 2023

(65) Prior Publication Data

US 2024/0108770 A1 Apr. 4, 2024

Related U.S. Application Data

(60) Division of application No. 17/334,778, filed on May 30, 2021, now Pat. No. 11,938,243, which is a
(Continued)

(51) Int. Cl.
*A61L 2/00* (2006.01)
*A61L 2/12* (2006.01)
(Continued)

(52) U.S. Cl.
CPC .................. *A61L 2/22* (2013.01); *A61L 2/12* (2013.01); *A61L 2/24* (2013.01); *A61L 2/26* (2013.01);
(Continued)

(58) Field of Classification Search
CPC .......... A61L 2202/14; A61L 2/12; A61L 2/18; A61L 2202/16; A61L 2202/25
(Continued)

(56) References Cited

U.S. PATENT DOCUMENTS 4,975,246 A 12/1990 Charm
6,039,921 A 3/2000 Boucher
(Continued)

FOREIGN PATENT DOCUMENTS

EP 2599506 A2 6/2013
EP 3354291 A1 8/2018
(Continued)

OTHER PUBLICATIONS

International Preliminary Report on Patentability (IPEA/KR) mailed on Jun. 30, 2021 for PCT/2020/024104 (with annex).
(Continued)

*Primary Examiner* — Monzer R Chorbaji
(74) *Attorney, Agent, or Firm* — Paradice & Li LLP; Anand S. Chellappa

(57) ABSTRACT

Mobile decontamination systems and microwave assisted decontamination methods for decontaminating a variety of contaminated surfaces disposed external to the system. The systems and methods include treating the surfaces with benign chemical formulations followed by exposing to microwave irradiation for short periods of time to achieve at least 6-log reduction in biological contaminants including viruses and spores of *B. anthracis*, *B. thuringiensis*, and *P. roqueforti*. The formulations include a percarbonate and surfactant in water.

19 Claims, 5 Drawing Sheets

Figure 1:
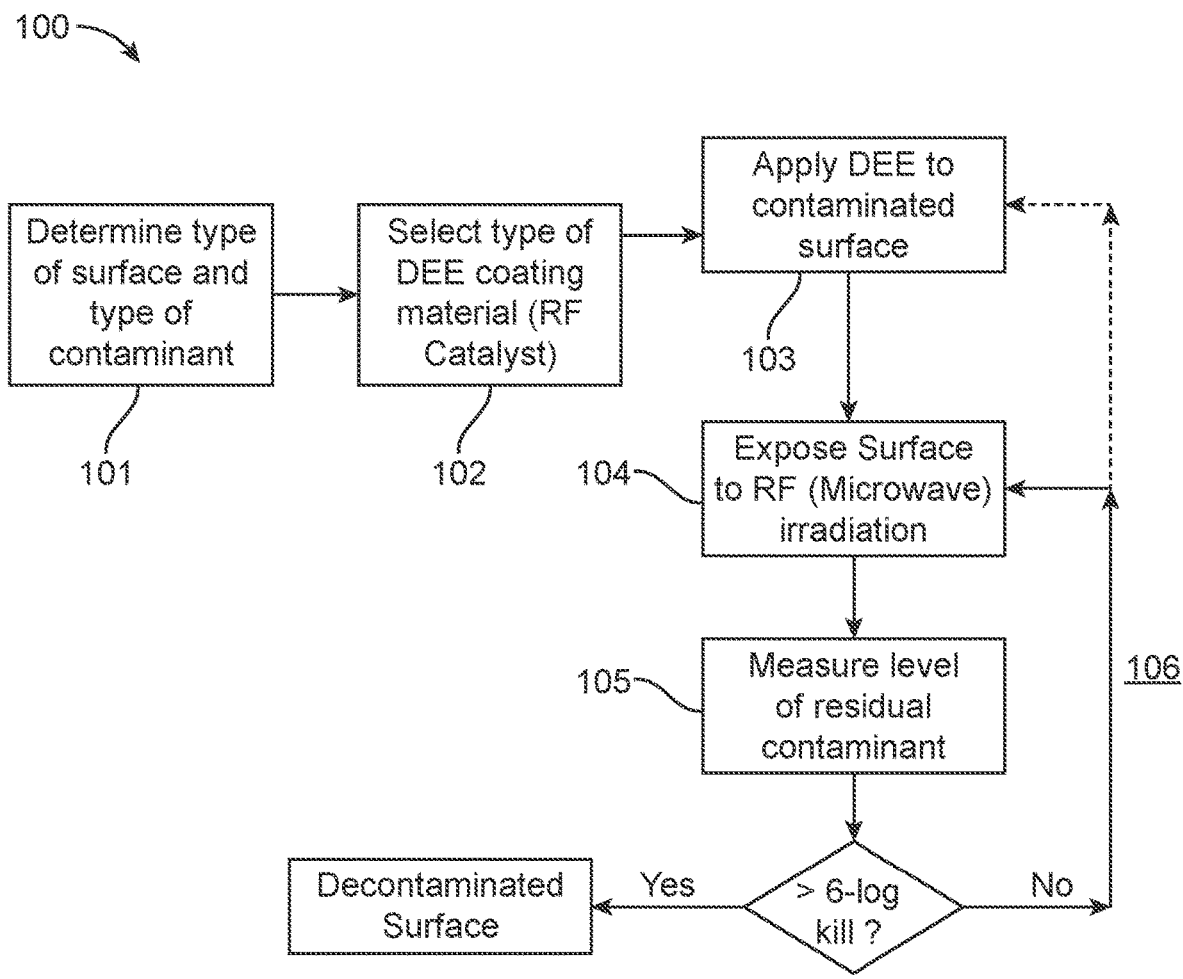
Figure 2:
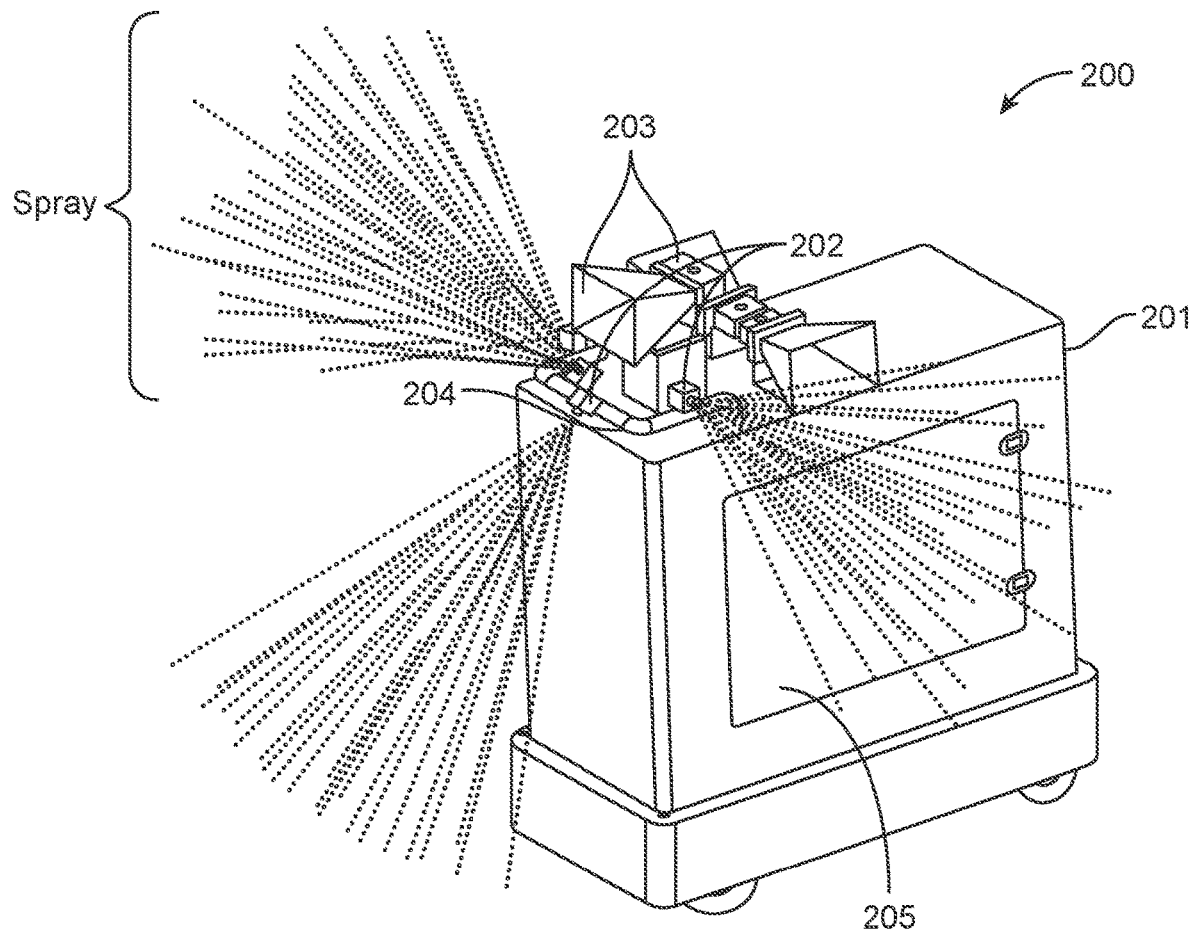
Figure 3:
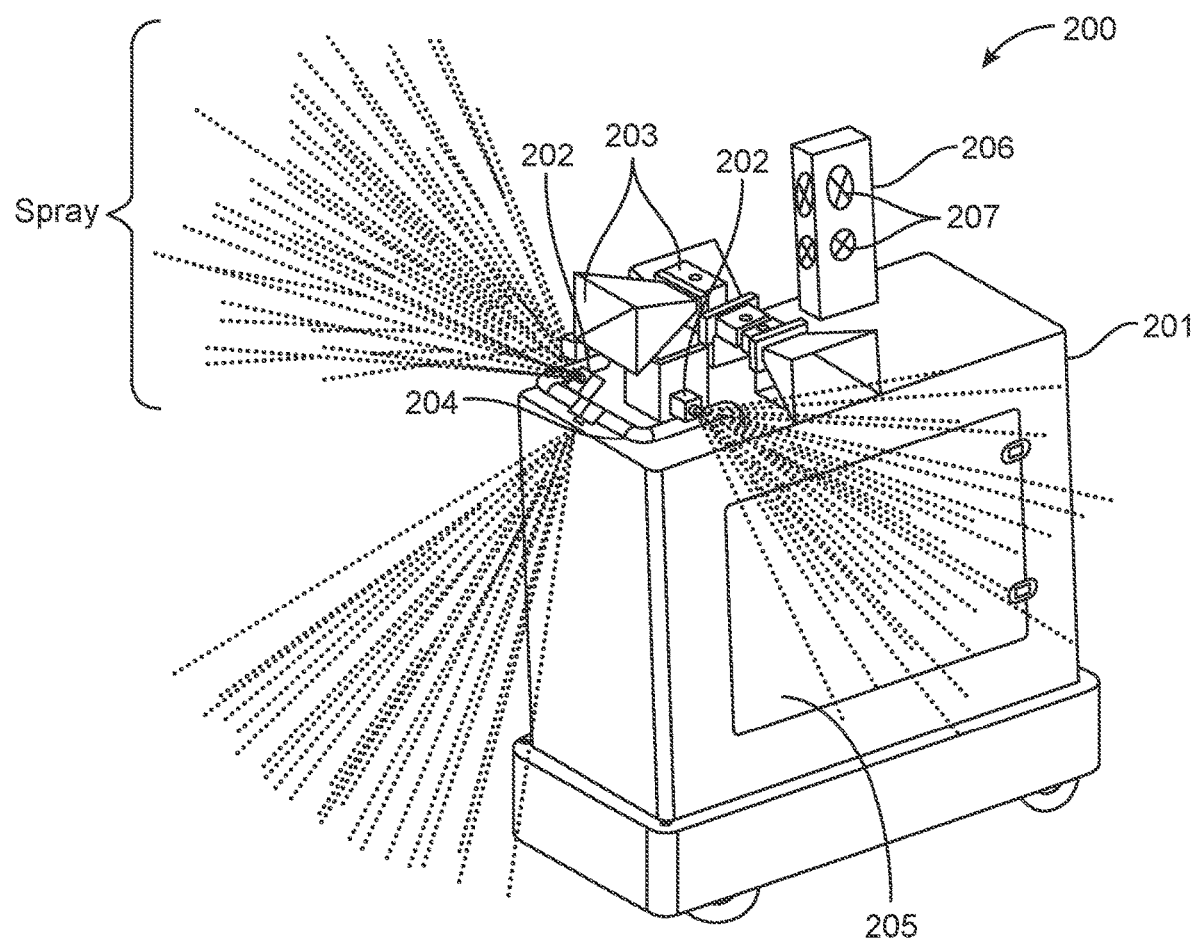

Related U.S. Application Data continuation-in-part of application No. PCT/US2020/024104, filed on Mar. 22, 2020.

(60) Provisional application No. 63/032,726, filed on Jun. 1, 2020, provisional application No. 62/822,782, filed on Mar. 22, 2019, provisional application No. 62/992,983, filed on Mar. 21, 2020.

(51) Int. Cl.
- *A61L 2/22* (2006.01)
- *A61L 2/24* (2006.01)
- *A61L 2/26* (2006.01)
- *B06B 1/00* (2006.01)

(52) U.S. Cl.
CPC ....... *A61L 2202/14* (2013.01); *A61L 2202/15* (2013.01); *A61L 2202/16* (2013.01); *A61L 2202/25* (2013.01)

(58) Field of Classification Search
USPC .......................................... 422/28, 128, 292
See application file for complete search history.

(56) References Cited

U.S. PATENT DOCUMENTS

| | | | |
|---|---|---|---|
| 6,521,178 | B1 | 2/2003 | Goldstein et al. |
| 6,797,242 | B2 | 9/2004 | Neumann et al. |
| 7,008,592 | B2 | 3/2006 | Sias et al. |
| 7,629,918 | B2 | 12/2009 | Brown et al. |
| 8,943,744 | B2 | 2/2015 | Cohen |
| 11,524,087 | B2 | 12/2022 | McCreery et al. |
| 2004/0261620 | A1* | 12/2004 | Thompson ................ A61L 9/20 96/16 |
| 2008/0260716 | A1 | 10/2008 | Kritzler et al. |
| 2010/0132735 | A1 | 6/2010 | Gaus et al. |
| 2010/0247403 | A1 | 9/2010 | Hancock |
| 2011/0064605 | A1* | 3/2011 | Hedman ................ A61L 9/015 422/1 |
| 2014/0205502 | A1 | 7/2014 | Park et al. |
| 2016/0271803 | A1* | 9/2016 | Stewart ................ B25J 11/0085 |
| 2017/0368217 | A1 | 12/2017 | Berentsveig et al. |
| 2018/0007922 | A1 | 1/2018 | Torngren et al. |
| 2018/0154030 | A1 | 6/2018 | Erickson et al. |
| 2018/0257308 | A1 | 9/2018 | Ahmad et al. |
| 2021/0290806 | A1 | 9/2021 | McCreery et al. |
| 2023/0042863 | A1 | 2/2023 | McCreery et al. |

FOREIGN PATENT DOCUMENTS

| | | |
|---|---|---|
| GB | 2463521 A | 3/2010 |
| JP | 2018534095 A | 11/2018 |
| WO | 9641500 A1 | 12/1996 |
| WO | 9925802 A1 | 5/1999 |
| WO | 2003015834 A1 | 2/2003 |
| WO | 2015123194 A1 | 8/2015 |
| WO | 2017053668 A1 | 3/2017 |

OTHER PUBLICATIONS

International Preliminary Report on Patentablility (IPEA/KR) mailed on Jul. 28, 2022 for PCT/US2021/035054. (with annex).

Lai, W. et al. "Decontamination of biological warfare agents by a microwave plasma torch," Physics of Plasmas 12, 023501 (2005).

N. van Doremalen, et al. Aerosol and surface stability of HCoV-19 (SARS-COV-2) compared to SARS-COV-1. N. Engl. J. Med. 2020; 382:1564-1567.

Shen, et al. "Highly Efficient Microwave-Assisted Fenton Degradation of Toluene Nitration Wastewater over Microwave-Responsive Catalyst of $Fe_3O_4$—BiOCl." ChemistrySelect, Research Article doi.org/10.1002/slct.202200804, pp. 1-10. (Year: 2022).

* cited by examiner

MOBILE SYSTEMS FOR MICROWAVE ASSISTED SURFACE DECONTAMINATION AND DECONTAMINATION METHODS

RELATED APPLICATIONS

This Patent application is a divisional of U.S. patent application Ser. No. 17/334,778 filed May 30, 2021, and entitled "MOBILE SYSTEMS FOR MICROWAVE ASSISTED SURFACE DECONTAMINATION AND DECONTAMINATION METHODS," which is related to and claims the benefit of U.S. Provisional Patent Application 63/032,726, filed Jun. 1, 2020, and entitled "Microwave Assisted Methods and Systems For Surface Decontamination," the disclosure of which is hereby incorporated by reference in its entirety. U.S. patent application Ser. No. 17/334,778 is a continuation-in-part of International Application No. PCT/US2020/024104, filed Mar. 22, 2020, which is related to and claims the benefit of U.S. Provisional Patent Application 62/822,782, filed Mar. 22, 2019, and entitled "Microwave Assisted Methods and Systems For Surface Decontamination," and U.S. Provisional Patent Application 62/992,983, filed Mar. 21, 2020, and entitled "Microwave Assisted Methods and Systems For Surface Decontamination," the disclosures of which are hereby incorporated by reference in each of their entireties.

FEDERALLY SPONSORED RESEARCH AND DEVELOPMENT

The disclosure was partly made with U.S. Government support under contract No. HSHQDC-14-C-00050 granted by the U.S. Department of Homeland Security. The U.S. Government may have certain rights in the disclosure.

FIELD

This disclosure relates to methods and systems for decontaminating a variety of contaminated surfaces in both enclosed structures and wide areas. In particular, the systems and methods include treating the surfaces with benign chemical formulations followed by exposing to radio frequency irradiation (microwaves) for short periods of time.

BACKGROUND

A recent report from the National Institutes of Health (NIH) and its partners (N. van Doremalen, et al., 2020) shows that the virus that causes coronavirus disease 2019 (CoVID-19) is stable for several hours to days in aerosols and on surfaces. The coronavirus 2 (SARS-CoV-2) was detectable in aerosols for up to three hours, up to four hours on copper, up to 24 hours on cardboard and up to two to three days on plastic and stainless steel. The results provide key information about the stability of SARS-CoV-2, which causes CoVID-19 disease, and suggests that people may acquire the virus through the air and after touching contaminated objects. On cardboard, the half-life of SARS-CoV-2 was longer than that of SARS-CoV-1. The estimated median half-life of SARS-CoV-2 was approximately 5.6 hours on stainless steel and 6.8 hours on plastic. Quick and effective surface decontamination methods are required to limit the spread of CoVID-19.

The commercial aviation industry suffered billions in lost revenue during the SARS (severe acute respiratory syndrome) epidemic. The only approved method for decontaminating commercial aircraft involves the wiping down of every single surface in the plane by hand using liquid disinfectants (e.g., diluted bleach) by personnel suited up in protective suits with respirators. It is a painstakingly slow process and is impractical if a large number of aircraft requires decontamination. Other market segments such as the travel and hospitality market have similar needs to treat contamination of cruise ships, buses, trains, and other shared environments. Decontamination of military aircraft using hot and humid air has been tested. Reports indicate that the destruction of spores using high temperature and humidity levels required treatment on the order of 3-4 days. This approach also damages critical systems within the aircraft. During pandemic or biological attack situations, there are major risks of contamination of aircraft or Aerial Point of Debarkation (APOD) sites. Conventional oxidative decontaminants have the potential to embrittle aircraft aluminum or damage sensitive equipment in APODs.

Turning to the healthcare market, cleaning and disinfection functions are done routinely throughout the healthcare industry. Patient rooms, surgery suites, and isolation rooms for highly infectious patients require routine disinfection or in some cases, complete sterilization. The target organisms are typically bacteria, bacterial spores and viruses as opposed to mold. The ventilation systems may also require periodic disinfection. Whole building decontamination is expensive and challenging. The Bio-response Operational Testing and Evaluation (BOTE) Project was a multi-agency effort that was designed to test and evaluate, at the scale of a moderately sized building, a response to a *B. anthracis* spore release from initial public health and law enforcement investigation through environmental remediation. First responders face decontamination or disinfection issues as well. Decontamination of ambulances that transport patients with infectious diseases such as Ebola Virus Disease or the patients infected by coronavirus types (e.g., CoVID-19 patients) is also challenging because ambulances should be remediated prior to being placed back into service.

Fumigants have been used to decontaminate surfaces exposed to agents released in enclosed structures, such as the Amerithrax attacks that was perpetrated through the mail in 2001. During the U.S. Hart Senate Office Building decontamination, a major challenge was the need to maintain a minimum temperature of 70° F. and minimum relative humidity of 65% RH for the decontaminant, chlorine dioxide (CD), to be stable and effective. At conditions, outside this range, CD decomposes easily to produce chlorine, which is highly reactive and causes damage to surfaces. Further, CD is toxic to humans. A CD concentration of about 700 ppm was used for many hours. The OSHA permissible exposure limit (PEL) for CD is 0.1 ppm, the 15-minute short term exposure limit (STEL) is 0.25 ppm, and the NIOSH immediately damaging to life and health (IDLH) level is 5 ppm. As a result of this clean-up, significant damage to the surfaces in the building was reported.

The use of other fumigants is also problematic. For example, vaporized hydrogen peroxide (VHP) at concentrations of 200 ppm is somewhat less toxic than CD with a PEL of 1 ppm, a STEL of 2 ppm, and an IDLH of 75 ppm. Other examples of fumigants for decontamination are methyl bromide and formaldehyde. Methyl bromide is a well-known, highly potent greenhouse gas and requires the structure to be fully covered to minimize release into the atmosphere. Formaldehyde has only been used in limited applications such as decontaminating small rooms or laboratory instruments. Formaldehyde is a well-known carcinogen, is toxic (PEL of 0.75 ppm, and STEL 2 ppm) and typically leaves a solid polymer residue that must be cleaned from all surfaces to prevent long term outgas sing. Fumigants are also not useful for surface decontamination in wide area outdoor release scenarios.

For decontaminating wide area (outdoor) surfaces, oxidation has been tried to deactivate bio-threat agents on surfaces. Oxidative agents include at least one of hydroxyl radicals that may be produced on-demand at the site, gaseous oxygen, ozone, hydrogen peroxide, hypochlorite (bleach such as sodium hypochlorite and calcium hypochlorite), and chlorine. These chemicals however damage surfaces and are generally toxic to humans. Because of these unfavorable after-effects, the U.S. DOD, for example, has tried biological decontamination of land vehicles using hot soapy water, and of airframe interiors using a combination of hot air and high humidity over long periods of time. These approaches are not effective in destroying biological contaminants. Further, if a wide area dissemination of bio-threat agent occurs, hazmat teams find it challenging to decontaminate their own equipment and vehicles.

Decontamination of wide areas surfaces has also been attempted by first exposing the surface to chemicals such as sodium hypochlorite (bleach) and then to microwave radiation to generate highly reactive oxidative species that kill biological agents. For example, 6-log kill (reduction, >99.999% reduction) of *Bacillus anthracis* (Sterne) spores on complex surfaces has been demonstrated by The Raytheon Company and the Los Alamos National Laboratory by spraying the surfaces with dilute household bleach (0.025% sodium hypochlorite) or carbon black followed by activation of the treated surface for a period of about 5 s to 120 s using 95 GHz irradiation. Greater than 6-log reduction in *B. anthracis* was seen at exposure times >5 s. In this hybrid approach, the chemicals used prior to exposing to radio frequency radiation such as microwaves may be viewed as directed energy enhancers ("DEE"). When exposed to RF irradiation, the DEE chemicals generate oxygen containing radicals which has biocidal properties and kills biological contaminants. These reactive species may be continuously generated by treating contaminated surfaces with DEE chemicals and exposing to RF radiation. This hybrid approach has two outstanding advantages over other technologies, namely, (1) it can use extremely low concentrations of decontaminant material which vastly lowers cost and mitigates materials compatibility and environmental contamination problems and, (2) the transient active biocide species (oxygen containing radicals) may be continuously regenerated to prevent the need for reapplication due to interaction with materials. However, bleach is harmful to surfaces. Further, carbon black has the tendency to penetrate into equipment (e.g., computers) found on surfaces and cause electrical short circuits because carbon black is conductive.

U.S. Pat. Pub. No. 20180007922, "METHOD AND SYSTEM FOR MICROWAVE DECONTAMINATION OF FOOD SURFACES," describes a method and a system for decontamination the surface of food items such as meat pieces. The method includes treating the food item and/or the meat piece with microwaves in the range of 0.5-18 GHz, such as 4-18 GHz. The method was used to treat meat pieces that were surface contaminated with *C. botulinum* spores or *C. botulinum* vegetative cells. U.S. Pat. No. 6,797,242, "SYSTEM FOR CHEMICAL AND BIOLOGICAL DECONTAMINATION" discloses a system that produces singlet delta oxygen that neutralizes chemical and biological contaminants. The system can decontaminate large quantities of contaminated air and is not limited by the humidity of the air. U.S. Pat. No. 7,629,918, "MULTIFUNCTIONAL RADIO FREQUENCY DIRECTED ENERGY SYSTEM" discloses a system including a radio frequency transmitter and antenna that directs high power electromagnetic energy towards a target sufficient to cause high energy damage or disruption of the target. U.S. Pat. No. 8,943,744, "APPARATUS FOR USING MICROWAVE ENERGY FOR INSECT AND PEST CONTROL AND METHODS THEREOF," discloses an apparatus for using microwave energy for treating a site infested with insects or other small pests. The apparatus includes a source of microwave energy connected to a power source and a power controller, a transmission element, and an antenna. Methods to use such an apparatus for treatment of an infected site is also disclosed. Lai et al. (2005) disclose a portable microwave plasma torch running with airflow for the decontamination of biological warfare agents. Emission spectroscopy of the plasma torch indicated the production of an abundance of reactive atomic oxygen that could effectively oxidize biological agents. *Bacillus cereus* was chosen as a simulant of *Bacillus anthracis* spores for biological agent in the decontamination experiments. Experimental results showed that all spores were killed in less than 8 s at 3 cm distance, 12 s at 4 cm distance, and 16 s at 5 cm distance away from the nozzle of the torch.

Subsequently, the threat from aerosolized biological agents remains a key concern of the U.S. Government because of the potentially dire consequences to life and property that may result from such an event. Two prime threat scenarios of particular concern are: (1) release of an agent inside an enclosed structure (e.g., office building, airport, mass transit facility) where HVAC systems could effectively distribute the agents through the entire structure and, (2) wide area release of an agent across an inhabited area such as a town or city. Exposure to the released aerosolized agent could lead to mass casualties. In a wide area release, it is extremely difficult to protect citizens from the initial exposure. Safe, effective and environmentally friendly solutions are needed to mitigate long term effects associated with re-aerosolization and exposure to agents deposited on surfaces and to minimize damage to the surfaces. Methods and systems that do not use harmful chemicals are needed to decontaminate surfaces, both in enclosed structures and wide areas, quickly, without any material damage to surfaces or causing side effects in humans, and at low cost. DEE chemical formulations with low chemical toxicity, minimal corrosion, and environmental acceptability are needed. At least 6-log reduction in biological contaminant is desired using low temperature, preferably close to ambient temperature, treatment methods.

BRIEF DISCLOSURE

Disclosed are example methods and systems for decontaminating a variety of surfaces in both enclosed structures and wide areas. In particular, the systems and methods include treating the surfaces with benign chemical formulations followed by exposing the surface to radio frequency irradiation (microwave) for short periods of time.

In some implementations an example method for treating contaminated surfaces disposed external to the system may include providing an example mobile system as disclosed herein for treating contaminated surfaces, spraying a directed energy enhancer ("DEE") formulation on to the contaminated surfaces to substantially coat the contaminated surfaces to form coated surfaces. The DEE formulation may include about 2.5 wt.-% PCSR in water. The coated surfaces may be exposed to microwave irradiation for a predetermined exposure time to substantially decontaminate the coated surfaces to yield treated surfaces. The treated surfaces may be characterized by a contaminant reduction of at least 6-log reduction. The DEE formulation may further include about 1 wt.-% of surfactant. The contaminated surfaces may include one or more of metal, concrete, plastic, or wood. The contaminated surfaces may include at least one of surfaces inside hospital rooms, aircrafts, and office buildings. The surface contaminants may include one or more of 229E (alpha coronavirus), NL63 (alpha coronavirus), OC43 (beta coronavirus), HKU1 (beta coronavirus), MERS-CoV, SARS-CoV, or SARS-Coronavirus-2. The microwave radiation may be characterized by a frequency of between about 2.35 GHz and about 2.65 GHz. The microwave radiation may be characterized by a frequency of about 2.45 GHz. The microwave radiation may be characterized by heat output of between about 500 W about 2000 W. The predetermined exposure time for microwave radiation exposure may be between about 10 s and about 45 s. The predetermined exposure time for microwave radiation may be between about 15 s and about 30 s.

In some implementations, an example microwave assisted surface decontamination method for treating surfaces contaminated with a contaminant may include spraying a DEE formulation on to the contaminated surfaces to substantially coat the contaminated surfaces to form coated surfaces. The DEE formulation may include about 2.5 wt.-% PCSR in water. The decontamination operation may continue with waiting for a predetermined hold time and exposing the coated surfaces to microwave radiation for a predetermined exposure time to substantially decontaminate the coated surfaces to yield treated surfaces. The treated surfaces may be characterized by a contaminant reduction of at least 6-log reduction. The predetermined hold time may be between about 15 s and about 45 s.

In some implementations, a DEE formulation for use in microwave assisted surface decontamination may include about 2.5 wt.-% PCSR in water. The DEE formulation may further include about 1 wt.-% surfactant in water.

Figure 4:
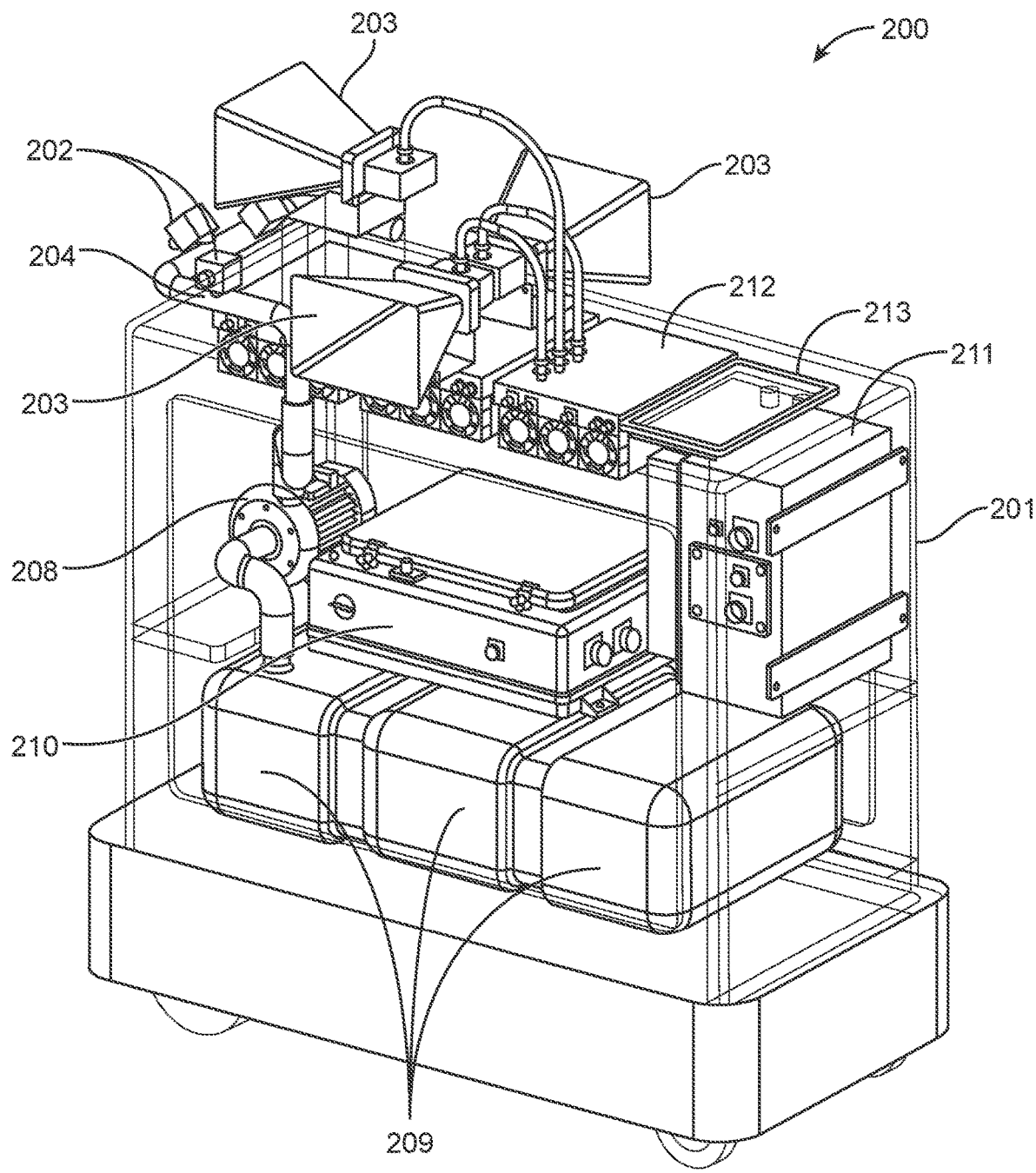

In some implementations, an example mobile system for treating contaminated surfaces disposed external to the system may include one or more on-board tanks for storing a directed energy enhancer (DEE) formulation in each tank, a sprayer subsystem including a plurality of nozzles removably connected to a fluid manifold and in fluid communication with the one or more storage tanks for spraying the DEE formulation at a predetermined spray rate and substantially coat the contaminated surfaces to form coated surfaces, a radio frequency (RF) subsystem including a microwave generator configured to generate microwave radiation of predetermined frequency and a plurality of pyramidal horn antennas to direct the microwave radiation to the coated surfaces, a mobility subsystem including at least one of an undercarriage having wheels powered by a motor, computer vision, GPS, ultrasonic proximity sensors, optical sensors, sonar sensors, and gyroscopes and a robotic platform control system, a power supply, and a control system disposed in bi-directional communication with the sprayer subsystem, RF subsystem, mobility subsystem, and power supply. The nozzles may include at least one of flat-fan nozzles, extended range flat-fan nozzles, even flat-fan nozzles, twin orifice-flat fan nozzles, flood nozzles, hollow-cone orifice nozzles, and full-cone orifice nozzles. The microwave RF radiation may be characterized by a frequency of between about 2.35 GHz and about 2.65 GHz. The microwave irradiation may be characterized by a frequency of about 2.45 GHz. The system may be configured to be remotely controlled by a human operator. The system may be configured to be substantially autonomously operated. The microwave generator may generate microwave RF radiation at a power density of between about 1 $W/cm^2$ and about 2 $W/cm^2$. The DEE formulation may include about 2.5 wt.-% PCSR in water.

The control system may be configured to control the movement of the robotic mobility platform using input from at least one of computer vision, GPS, ultrasonic proximity sensors, optical sensors, sonar sensors, and gyroscopes. The control system may be configured to control at least one of the power supply to the microwave generator, the transfer of predetermined dosage of DEE formulation from the tank to the plurality of nozzles, the focusing of the plurality of nozzles to ensure coating of the contaminated surface, the transmission of microwave radiation from the microwave generator through the plurality of horn antennas, and the focusing of the microwave radiation on to the coated surface. The control system may be further configured to measure the amount of DEE remaining in the one or more tanks using at least one of initial amount of DEE formulation in the tanks, spray rates from the one or more nozzles and spraying time corresponding to the one or more spray rates. The system may further include data acquisition components and data transfer components for transferring data to a remote server. Data may include at least one of the composition of DEE formulation, amount of DEE formulation used for treating a contaminated surface, amount of DEE formulation remaining in the one or more tanks, frequency of microwave radiation used, power density of microwave radiation, microwave radiation treatment time, and type of contaminant. The system power supply may be capable of electrical communication with at least one of the power supplies available within an aircraft and power supplies available at ground support when the aircraft is parked at an airport including an aircraft maintenance hangar. The system may be powered by a suitable battery pack disposed onboard the system.

Other features and advantages of the present disclosure will be set forth, in part, in the descriptions which follow and the accompanying drawings, wherein the preferred aspects of the present disclosure are described and shown, and in part, will become apparent to those skilled in the art upon examination of the following detailed description taken in conjunction with the accompanying drawings or may be learned by practice of the present disclosure. The advantages of the present disclosure may be realized and attained by means of the instrumentalities and combinations particularly pointed out in the appendant claims.

DRAWINGS

The foregoing aspects and many of the attendant advantages of this disclosure will become more readily appreciated as the same becomes better understood by reference to the following detailed description, when taken in conjunction with the accompanying drawings, wherein:

FIG. 1 shows a schematic diagram of an example microwave assisted method for surface decontamination, according to some implementations.

FIG. 2 shows a perspective view of an example microwave assisted device for surface decontamination, according to some implementations.

FIG. 3 shows a perspective view of another example microwave assisted device for surface decontamination, according to some implementations.

FIG. 4 shows a perspective view (exploded) of an example microwave assisted decontamination device with graphical user interface, according to some implementations.

Figure 5:
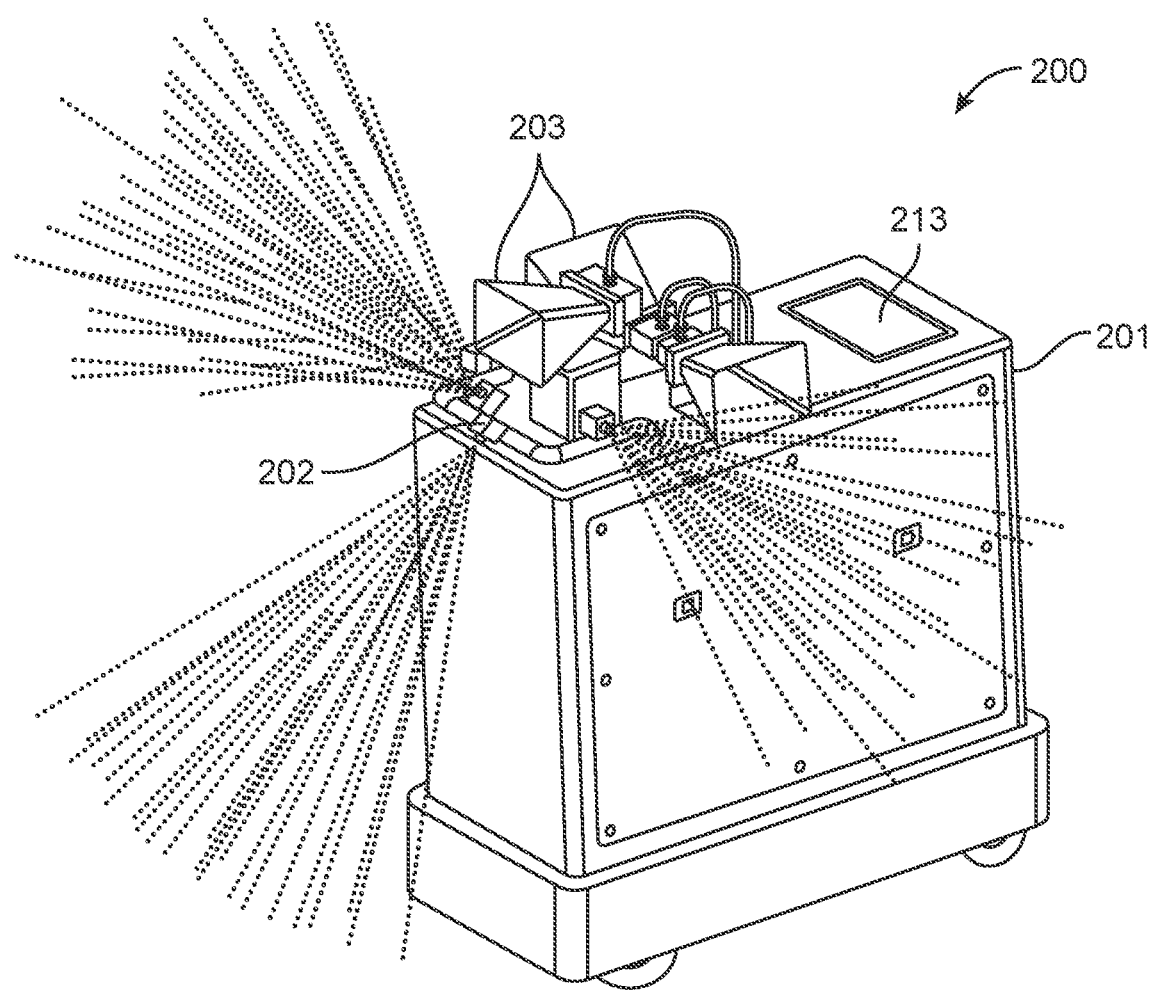

FIG. 5 shows a perspective view of an example microwave assisted decontamination device with graphical user interface, according to some implementations.

All reference numerals, designators and callouts in the figures are hereby incorporated by this reference as if fully set forth herein. The failure to number an element in a figure is not intended to waive any rights. Unnumbered references may also be identified by alpha characters in the figures and appendices.

The following detailed description includes references to the accompanying drawings, which form a part of the detailed description. The drawings show, by way of illustration, specific embodiments in which the pilot assembly and methods may be practiced. These embodiments, which are to be understood as "examples" or "options," are described in enough detail to enable those skilled in the art to practice the present invention. The embodiments may be combined, other embodiments may be utilized, or structural or logical changes may be made, without departing from the scope of the invention. The following detailed description is, therefore, not to be taken in a limiting sense and the scope of the invention is defined by the appended claims and their legal equivalents.

In this document, the terms "a" or "an" are used to include one or more than one, and the term "or" is used to refer to a nonexclusive "or" unless otherwise indicated. In addition, it is to be understood that the phraseology or terminology employed herein, and not otherwise defined, is for the purpose of description only and not of limitation. Unless otherwise specified in this disclosure, for construing the scope of the term "about," the error bounds associated with the values (dimensions, operating conditions etc.) disclosed is ±10% of the values indicated in this disclosure. The error bounds associated with the values disclosed as percentages is ±1% of the percentages indicated. The word "substantially" used before a specific word includes the meanings "considerable in extent to that which is specified," and "largely but not wholly that which is specified."

DETAILED DISCLOSURE

Particular aspects of the invention are described below in considerable detail for the purpose for illustrating the compositions, and principles, and operations of the disclosed methods and systems. However, various modifications may be made, and the scope of the invention is not limited to the example aspects described.

Treating contaminated surfaces with example DEE formulations disclosed herein followed by exposure to RF irradiation may be used to destroy viruses such as the MS2 bacteriophage, which is commonly used as a surrogate for pathogenic human viruses such as SARS-Coronavirus-2. These example treatment methods may be used to destroy viruses such as the MS2 bacteriophage, which is commonly used as a surrogate for pathogenic human viruses such as SARS-Coronavirus-2. The viruses may include one or more of 229E (alpha coronavirus), NL63 (alpha coronavirus), OC43 (beta coronavirus), HKU1 (beta coronavirus), MERS-CoV, SARS-CoV, or SARS-Coronavirus-2. MS2 bacteriophage viruses are considerably more difficult to inactivate or destroy than the enveloped viruses such as SARS-Coronavirus-2. Without being bound by any particular theory, an MS2 bacteriophage may infect a bacterial host such as *Escherichia coli*. Once inside the host cell, it may hijack the host cell and use the cell's resources to multiply into new phages. Upon completion of MS2 phage assembly, the host cell lyses. The DEE formulations disclosed herein are effective for destroying viruses on a variety of surfaces when treated surfaces are exposed to RF radiation. Example DEE formulations for killing viruses may include about 2.5 wt.-% percarbonate based stain remover (PSCR) in water.

An example PCSR is commercially available OxiClean (Church & Dwight Co., Inc.). The PCSR preferably includes about 66 wt.-% sodium percarbonate (e.g., $2Na_2CO_3$: $3H_2O_2$) and about 34 wt.-% sodium carbonate. The surfaces treated with the example DEE formulation may then be exposed to about 2.45 GHz RF radiation for between about 10 s and about 45 s. Alternately, the surfaces treated with the example DEE formulation may be exposed to about 2.45 GHz RF radiation for between about 15 s and about 30 s. Additional details are provided in Example 1 in this disclosure. DEE formulations may also include copper and iron salts in water. Further, example DEE formulations for decontamination of surfaces contaminated with viruses may be bleach free. Example DEE formulations for virus decontamination may be free of surfactants. For decontamination of porous surfaces such as wood contaminated with viruses, example DEE formulations may include a surfactant to ensure penetration of DEE formulations into the pores. An example surfactant may include commercially available Tween 80 (Sigma Aldrich) surfactant, which is a polyethylene sorbitol ester that is also known as Polysorbate 80, PEG (80) sorbitan monooleate, and polyoxyethylenesorbitan monooleate. Tween 80 is used in detergents, soaps, cosmetics, mouthwash and ice cream and is a substantially benign chemical. The surfactant may have a calculated molecular weight of 1310 Daltons. Typically, the fatty acid composition is approximately 70 wt.-% oleic acid, with the balance being primarily linoleic, palmitic, and stearic acids. The oleic acid concentration is typically ≥58.0 wt.-%. The example DEE formulations and treatment methods may be used to decontaminate surfaces contaminated by pathogenic human viruses such as the SARS-Coronavirus-2.

Disclosed is an example mobile decontamination system 200 (FIGS. 2-5) that may be in the form of a mobile cart 201. The system may include a container (not shown) for holding a predetermined amount of DEE formulation and fluidic components (e.g., pumps, valves, and the like) to transfer the DEE formulation from the container to manifold 204, which is in fluid communication with one more spraying nozzles 202. An example DEE formulation includes about 2.5 wt.-% percarbonate based stain remover (PSCR) in water. An example PCSR is commercially available OxiClean (Church & Dwight Co., Inc.). Another example DEE formulation includes about 2.5 wt.-% PCR and about 1 wt.-% surfactant in water. The surfactant spreads the chemical over surfaces. An example surfactant may include commercially available Tween 80 (Sigma Aldrich) surfactant. The orientation of nozzles 202 may be adjusted to ensure that the contaminated surface may be quickly and completely (or substantially completely) exposed to a spray of DEE formulation. Microwave irradiation (e.g., at about 2.35 GHz to about 2.65 GHz frequency and preferably at about 2.45 GHz frequency) from a microwave generator (not shown) may be directed to the sprayed surface using pyramidal horn antennas 203. The orientation of the antennas may also be adjusted/varied to quickly treat the DEE-sprayed contaminated surface to irradiation. The DEE formulation container and microwave generator may be housed within cart 201 and accessed using door 205. The cart may incorporate a fan system 206 (FIG.

3) including one or more fans 207 to disperse the DEE formulation that exits the one or more nozzles 202. Spraying nozzles 202 may include small scale agricultural sprayers or nozzles. The flow or spray patterns from these nozzles are well characterized and different types of nozzles may be selected to produce the desired precise spray patterns required to quickly cover or treat a contaminated surface or area with DEE formulation. Nozzle types may include but are not limited to, flat-fan nozzles, extended range flat-fan nozzles, even flat-fan nozzles, twin orifice-flat fan nozzles, flood nozzles, hollow-cone orifice nozzles, and full-cone orifice nozzles. Example system 200 may include a sprayer subsystem including nozzles 202, pump 208, fan system 206, manifold 204, and DEE formulation container 209 (FIG. 4). More than one container 209 may be used in example system 200. Pump 208 may include at least one of a centrifugal pump, diaphragm pump, piston pump, roller pump, and irrigation-injection pump.

One or more fans 207 may be removably installed on the cart for decontamination of small spaces in enclosed structures. Alternately, fan system 206 may be tethered to the cart for decontamination of larger spaces or wide areas. The tether is configured to provide bidirectional communication with the control system (system master controller). The air flow rate output from one or more fans 207 may be scaled in size depending on the size of the space that is to be decontaminated. Preferably, the air flow rating of the one or more fans 207 may be between about 150 cubic feet per minute and about 250 cubic feet per minute and may be varied to optimize DEE formulation dispersion and deposition on contaminated surfaces. In addition to the one or more fans, fan system 206 may include power components for operating the fans and control components for communicating with a system master controller. Components such as a power source, magnetron, controllers and microwave transmission elements, and controllers for transfer and spraying of the DEE formulations are preferably housed within cart 201. The master controller may control cart movement, spraying, fan system operation and microwave treatment steps.

Commercially available magnetrons such as resonant cavity magnetrons designed for household microwave ovens rated at 500 W to 2 kW may be used. Example system 200 may be used to substantially decontaminate surfaces in enclosed areas (e.g., rooms). The system may be scaled-up to treat surfaces in wide areas (e.g., 1 km$^2$) also. With an example DEE formulation including about 1 wt.-% surfactant and about 1 wt.-% PCSR in water, about 2500 kg of DEE (2000 kg of solid PCSR such as OxiClean and 500 kg of Tween 80 surfactant) formulation may be sufficient to decontaminate an area of 1 km$^2$, which represents a 10× reduction in chemical required if a conventional chemical such as Spor-Klenz is used without any microwave irradiation. Spor-Klenz may include of about 6% hydrogen peroxide solution or about 0.525% hypochlorite solution (Steris Life Sciences) is used. For an example DEE formulation including 0.06 M copper (II) chloride in water, 2500 kg of copper (II) chloride may be sufficient to substantially decontaminate surfaces in a 1 km$^2$ area. The example DEE formulations disclosed herein are benign to both surfaces and humans. The DEE formulation sprayer may be in the form of a fogger. Antennas 203 may be operated using RF control system 210, power converter 211 and one or more power supplies 212. Example cart 200 may include a RF subsystem including antennas 203 and one or more power supplies (microwave generator) 212. Control system 210 may be used to adjust parameters including at least one of frequency of RF radiation, frequency band of RF irradiation, power density (W/cm$^2$ or mW/cm$^2$), and RF irradiation exposure time.

Cart 201 may be configured to be remotely operated by a human operator. The cart may be substantially autonomous; that is, it may be capable of sensing its environment and moving with minimal human input. It may use a plurality of sensors for sensing its surroundings and for navigation, that include, but are not limited to, radar, computer vision, GPS, ultrasonic proximity sensors, optical sensors, sonar and gyroscopes. A robotic mobility subsystem may include sensors, motor, and undercarriage including wheels in cart 201. Cart 201 and the sprayer subsystem, RF subsystem and mobility subsystem may be controlled using graphical user interface 213 and control system 210 that are in bidirectional communication with each other. System 200 may be built on a robotic platform such as a six-wheel drive (6WD) all terrain robotic platform (SuperDroid Robots, Fuquay-Varina, NC). The motors and drive train of the robotic platform may be controlled using a robotic platform control system which may be configured to take instructions from and communicate with control system 210. The sprayer subsystem and control system 210 may be configured to measure amount of DEE remaining in container 209 using at least one of initial amount of DEE formulation, one or more spray rates from nozzles 202 and spraying time corresponding to the one or more spray rates. During treatment of a surface, spray rate may be constant or may be varied using a predetermined spraying protocol. Upon reaching a predetermined DEE consumption control system 210 may provide an alert via user interface 213 to either change out container 209 or refill container 209. Power converter 211 may be used to provide power to the robotic mobility subsystem using for example 100 V, 400 Hz power available on military and commercial aircraft or 28 VDC on military aircraft. DEE containers 209, control system 210, microwave generators 213 and power converter 211 may be housed within cart 201 (FIGS. 4-5). In another example cart 201 including a plurality of DEE formulation containers 209, one or more different DEE formulations may be provided in the one or more containers.

Microwave generators that produce microwave radiation at about 2.45 GHz are commercially available. For example, such generators are used in household microwave ovens. For decontamination of aircrafts, a key concern for selecting the microwave frequency and power density is to ensure that aircraft electronics are not damaged during the decontamination process. For example, military aircraft electronics must be tested to meet MIL-STD-461G standards. Radars, communication systems, and jammers are all part of the airspace under combat operations. The ASR-9 Aircraft Surveillance Radar used by the Federal Aviation Administration operates at between about 2.7 GHz and about 2.9 GHz. The RF power density required using commercial microwave generators that output microwave RF radiation at about 2.45 GHz may be characterized by an upper limit of between about 1 W/cm$^2$ and about 2 W/cm$^2$. Since RF power density decreases as a function of 1/R$^2$, where R is the distance from the RF generator, assuming a power density of 1 W/cm$^2$ at 10 cm away from the contamination surface in the aircraft cabin, the power density 10 m away will be 0.1 mW/cm$^2$, which is significantly lower than the transmitted power density near a cell phone.

FIG. 1 shows a schematic drawing of an example method 100 for microwave assisted surface decontamination using the example DEE formulations disclosed herein. The type of surface and nature of decontaminant may be determined in step 101. The approximate concentration of the contaminant may also be determined in step 101. Example surfaces may include at least one of metal, concrete, plastic, and wood. Example contaminants (spore and/or vegetative cells) may include at least one of *B. anthracis*, *B. thuringiensis*, and *P. roqueforti*. Based on the information gathered in step 101, an example DEE formulation as disclosed herein may be selected for surface coating in step 102. In addition to the previously disclosed DEE formulations, another DEE formulation that is effective for decontaminating various types of surfaces may include PCSR, copper (II) chloride and bleach in water. The DEE formulation may include about 1 wt.-% to about 10 wt.-% PCSR, about 0.05 M to about 0.1 M copper (II) chloride, and at least about 100 ppm bleach, the balance being water. Another DEE formulation may include about 1 wt.-% to about 10 wt.-% PCSR, about 0.06 M copper (II) chloride, and at least about 250 ppm bleach, the balance being water. The bleach content is preferably between about 250 ppm and about 1000 ppm.

The selected DEE formulation may then be applied to the contaminated surface in step 103 by spraying or other suitable means. Subsequently, the contaminated surface coated with the DEE formulation may be exposed to radio frequency (microwave) irradiation in step 104. The method may include a holding time defined as the time period between the surface coating with the DEE formulation and exposure of the coated surface to RF irradiation in step 104. The frequency of irradiation is preferably 2.45 GHz that may be generated using commercially available microwave generators. The coated surface may be exposed to irradiation for at least 10 s. The exposure time may be between about 10 s and about 120 s. Alternately, the exposure time may be between about 30 s and about 60 s. At least one of a sample of the treated surface and one or more calibrated test sample strips may be analyzed in step 105 to determine the concentration of the contaminant. The one or more test sample strips may be placed adjacent to the surface being decontaminated. Examples of test sample strips, include but are not limited to, biological indicator spore strips provided by Mesa Labs (Bozeman, MT) If at least 6-log reduction in the contaminant is realized, the surface may be deemed to be decontaminated and method 100 may be stopped. If step 105 indicates that additional treatment is required, at least one of steps 103 and 104 may be repeated in step 106. In step 106, the DEE formulation may be modified (e.g., an alternate DEE formulation may be used) to enhance the destruction of surface contaminants. The time period for microwave irradiation exposure may also be increased to achieve at least 6-log reduction of the biological contaminant.

Example directed energy enhancers ("DEE") generate reactive oxidative species (oxygen radicals that include, but are not limited to, singlet oxygen, OH, OOH radicals and the like) when exposed to radio frequency irradiation. These oxidative species subsequently destroy biological agents that include, but are not limited to, *Bacillus anthracis* (anthrax,) either in spore or vegetative species form and mold (e.g. *Penicillium roqueforti*). Spores are generally resistant to heat, dessication, chemicals, and radiation. Bacteria can form endospores in approximately 6 to 8 h after being exposed to adverse conditions. The normally-growing cell that forms the endospore is called a vegetative cell. Spores are metabolically inactive and dehydrated.

Example DEE chemical compositions may include at least one of copper (II) chloride, ascorbic acid, and a salt in water. The salt concentration may be between about 0.5 M and about 1.5 M and preferably about 1 M. 1 M generally refers to 1 mole of solute in 1 liter of solution. The salt may include sodium chloride. Copper (II) chloride dihydrate may be used to generate copper (II) ions in solution. The concentration of copper (II) chloride may be between about 0.05 M and about 1 M, and preferably between about 0.06 M and 0.6 M. The concentration of ascorbic acid may be about 1 M. These chemicals are commonly available food additives, household chemicals, and approved pesticides and fungicides. For example, the copper salt may be a common biocidal/fungicide agent qualified for use with certified organic foods. Ascorbic acid is a chemical component in Vitamin C. Without being bound by any theory, these example compositions are highly effective DEE chemical formulations because they generate reactive oxidative species when exposed to radio frequency (microwave) radiation.

In addition to copper (II) salts, other salts may be used to generate metal ions in solutions. Example metal salts include, but are not limited to, at least one of, or a mixture of casserite (tin oxide), manganite (manganese oxide), transition metal oxides including iron, chromium and cobalt oxides, nickel oxides, zinc oxides, lanthanide oxides, semiconductors such as p-doped and n-doped silicon, gallium arsenide, indium tin oxide, silicon carbide, and refractory metal nitrides and oxides.

Another example DEE chemical composition may include about 0.6 M copper (II) chloride and about 0.1 M ascorbic acid in water. Another example DEE chemical composition may include about 0.6 M copper (II) chloride, about 0.1 M ascorbic acid, and about 1 wt.-% surfactant, the remaining being water. Another example DEE chemical composition may include about 0.6 M copper (II) chloride, about 0.1 M ascorbic acid, about 1 wt.-% surfactant, and about 1 M salt in water.

Another example DEE chemical composition may include at least one of a surfactant and percarbonate based stain remover ("PCSR"). An example PCSR is commercially available OxiClean (Church & Dwight Co., Inc.). The PCSR preferably includes about 66 wt.-% sodium percarbonate (e.g., $2Na_2CO_3:3H_2O_2$) and about 34 wt.-% sodium carbonate. The surfactant concentration in example DEE formulations may be between about 1 wt.-% and 10 wt.-% and is preferably about 1 wt.-%. The PCSR concentration in example DEE formulations may be between about 1 wt.-% and about 10 wt.-%.

Another example DEE formulation may include at least one of copper (II) chloride, surfactant, PCSR, and sodium chloride in water. The sodium chloride concentration in the DEE formulation may be between about 0.5 M and about 1.5 M, and preferably about 1 M. The concentration of copper (II) chloride may be between about 0.05 M and about 1 M. The surfactant concentration may be between about 0.5 wt.-% and about 1 wt.-%. The surfactant concentration may be about 1 wt.-%. The PCSR concentration may be between about 1 wt.-% and about 10 wt.-%. Another example DEE composition may include about 0.06 M copper (II) chloride, about 1 wt.-% surfactant, between about 1 wt.-% and about 10 wt.-% PCSR and about 1 M salt in water. The salt may include sodium chloride.

Another example DEE composition may include at least one of a surfactant and bleach in water. An example bleach is Concentrated Clorox Regular Bleach, which includes about 6 wt.-% sodium hypochlorite (NaOCl). The surfactant concentration may be between about 0.5 wt.-% and about 1 wt.-%. The bleach concentration may be between about 1 wt.-% and 10 wt.-%.

Another example composition may include at least one of copper (II) chloride, a surfactant, bleach, and sodium chloride in water. The surfactant concentration may be between about 0.5 wt.-% and about 1 wt.-%. The bleach composition may be between about 1 wt.-% and 10 wt.-%. The sodium chloride composition may be between about 0.5 M and about 1 M. The copper (II) chloride concentration may be between about 0.05 M and 1 M. Another example composition may include about 0.06 M copper (II) chloride, about 1 M sodium chloride, about 1 wt.-% surfactant and between about 1 wt.-% and about 10 wt.-% bleach, in water.

Another example composition may include at least one of copper (II) chloride, ascorbic acid, and surfactant in water. The surfactant concentration may be between about 0.5 wt.-% and about 1 wt.-%. The ascorbic acid concentration may be between about 0.01 M and about 1 M. The copper (II) chloride concentration may be between about 0.05 M and 1 M. Another example DEE composition may include about 0.06 M copper (II) chloride in water. Another example DEE composition may include about 0.06 M copper (II) chloride, about 1 M sodium chloride, and about 0.1 M ascorbic acid.

Another example composition may include at least one of copper (II) chloride, hydrogen peroxide, and surfactant in water. The surfactant concentration may be between about 0.5 wt.-% and about 1 wt.-%. The hydrogen peroxide concentration may be between about 0.01 M and about 1 M. The copper (II) chloride concentration may be between about 0.05 M and 1 M. Another example composition may include about 0.06 M copper (II) chloride, about 1 M sodium chloride, about 1 wt.-% surfactant, and about 0.1 M hydrogen peroxide.

Another example DEE composition may include at least one of a surfactant and PCSR in water. The surfactant concentration may be between about 0.5 wt.-% and about 1 wt.-%. The PCSR concentration may be between about 1 wt.-% and about 10 wt.-%. Another example composition may include about 1 wt.-% surfactant and about 10 wt.-% PCSR in water. Another example composition may include about 1 wt.-% surfactant and about 1 wt.-% PCSR in water.

The microwave radiation may have a frequency of less than about 300 MHz to at least about 300 GHz, such as from about 300 MHz to about 300 GHz, from about 1 GHz to about 125 GHz, or from about 2.4 GHz to about 95 GHz. The frequency may be substantially a single frequency, such as, for example, about 2.4 GHz, about 10 GHz, about 50 GHz, or about 95 GHz. Alternatively, the frequency may vary across a range during an exposure time period, such as from about 1 GHz to about 125 GHz, or from about 2.4 GHz to about 95 GHz. In some embodiments, about 2.45 GHz is used to treat extended surfaces such as the ground or building surfaces. In other embodiments, about 95 GHz is used to treat delicate and/or surfaces with complex shapes.

The Raytheon Company has developed a series of full scale and field deployable 95 GHz systems in support of the Active Denial System (U.S. DOD non-lethal weapons program). These systems may be used for decontaminating surfaces using the example methods disclosed herein. The 95 GHz systems are characterized by output power of 100 W (watts), 400 W, and 100,000 W. The 100 W system is a fixed focus and fixed power output continuous wave system. Power density may be adjusted by varying the distance from the target to the antenna. The 400 W system is variable focus and variable power, pulsed output system and average power may be varied by changing the duty cycle. The 100 kW system is a large-vehicle mounted system with considerable range (in excess of 500 m), and with the ability to change its power output.

Without being bound by any particular theory, irradiation of the example DEE formulations sprayed on to the contaminated surface may generate at least one of highly reactive singlet oxygen and hydroxyl radicals (including, but not limited to OH, OOH radicals), possibly by the decomposition of hydrogen peroxide released from PCSR in solution, which destroys biological contaminants. Copper (II) chloride may act as a catalyst for peroxide decomposition following a chloride-accelerated copper Fenton type process wherein copper may transition from $Cu^{2+}$ to various oxidation states (redox mechanism) during the decomposition of the peroxide and is continuously regenerated in the process. The decomposition of hydrogen peroxide using transitional metal elements is commonly known as Fenton chemistry. $Cu^{2+}$ may be oxidized to $Cu^{3+}$ during peroxide decomposition upon microwave irradiation and reduced back to $Cu^{2+}$. Alternately, $Cu^{2+}$ may be reduced to $Cu^+$ and re-oxidized to $Cu^{2+}$ following a Cu-Fenton process. Microwave irradiation is believed to accelerate the underlying redox chemistry.

The example decontamination systems and methods may be used to mitigate insect infestation in the hospitality market in an environmentally friendly manner. Of particular interest is bedbug (*Cimex lectularius*) infestation remediation. Further, the example decontamination systems and methods may be used for hospital room decontamination, defense department equipment decontamination, commercial aircraft decontamination, and first responder/Hazmat equipment decontamination including when the contaminant is a virus such as the CoVID-19 coronavirus.

Contaminated surfaces include, but are not limited to concrete, wood, soil, galvanized metal, glass, plastic, and painted wallboard. These surfaces may be treated using the methods disclosed herein to achieve at least 6-log reduction in biological contaminant such as the anthrax simulant *B. thuringiensis*. The decontamination methods may be effective over a wide range of ambient temperature and humidity and in particular, at low temperature/low humidity (about 0° C. to about 25° C. and relative humidity of about 5% to about 40% RH), ambient temperature/medium humidity (about 20° C. to about 30° C. and 40%-50% RH), and high temperature/high humidity conditions (about 30° C. to about 50° C. and relative humidity of about 50% to about 95% RH).

EXAMPLE

Example 1: Destruction of Ms2 Bacteriophage Virus Using Example Dee Formulations and Exposure to about 2.45 Ghz RF (Microwave) Radiation Plaque assays for active MS2 bacteriophage virus (ZeptoMetric Corp., Catalog No. 0810066) enumeration were carried out using *E. coli* host cell strain C3000 (ATCC 15597). Briefly, MS2 bacteriophage was pipetted onto glass disc coupons including *E. coli* grown on an agar medium to mimic a common surface in buildings, public places, and the like and allowed to dry. The glass discs were treated with an example DEE formulation including about 2.5 wt.-% percarbonate based stain remover (PSCR) in water. An example PCSR is commercially available OxiClean (Church & Dwight Co., Inc.). The PCSR preferably includes about 66 wt.-% sodium percarbonate (e.g., $2Na_2CO_3:3H_2O_2$) and about 34 wt.-% sodium carbonate. The glass discs were then exposed to about 2.45 GHz RF microwave radiation for between about 15 s and about 30 s. With this treatment, >6-log reduction in MS2 was observed indicating that the MS2 virus was inactivated with a high level of efficacy at both 15 s and 30 s treatment time periods. Control tests were done using glass discs with MS2 which were treated with water. Even on exposure to about 2.45 GHz RF radiation, no reduction in MS2 virus counts were observed. Similarly treating the glass discs with MS2 with the example DEE formulation including about 2.5 wt.-% PSCR did not show any significant reduction in virus count when the discs were not exposed to about 2.45 GHz RF radiation.

The Abstract is provided to comply with 37 C.F.R. § 1.72(b), to allow the reader to determine quickly from a cursory inspection the nature and gist of the technical disclosure. It should not be used to interpret or limit the scope or meaning of the claims.

Although the present disclosure has been described in connection with the preferred form of practicing it, those of ordinary skill in the art will understand that many modifications can be made thereto without departing from the spirit of the present disclosure. Accordingly, it is not intended that the scope of the disclosure in any way be limited by the above description.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this disclosure is entitled. It should be understood that all actions may be expressed as a means for taking that action or as an element which causes that action. Similarly, each physical element disclosed should be understood to encompass a disclosure of the action which that physical element facilitates.

In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Further, the use of the transitional phrase "comprising" is used to maintain the "open-end" claims herein, according to traditional claim interpretation. Thus, unless the context requires otherwise, it should be understood that variations such as "comprises" or "comprising," are intended to imply the inclusion of a stated element or step or group of elements or steps, but not the exclusion of any other element or step or group of elements or steps. Such terms should be interpreted in their most expansive forms so as to afford the applicant the broadest coverage legally permissible.

REFERENCES

1. Lai W. et al. "Decontamination of biological warfare agents by a microwave plasma torch," Physics of Plasmas 12, 023501 (2005).
2. N. van Doremalen, et al. Aerosol and surface stability of HCoV-19 (SARS-CoV-2) compared to SARS-CoV-1. N. Engl. J. Med. 2020; 382:1564-1567.

What is claimed is:

1. A method for treating contaminated surfaces, the method including:
   providing a mobile decontamination system disposed as a mobile cart for housing:
   one or more on-board storage tanks for storing a directed energy enhancer (DEE) formulation in each tank;
   a sprayer subsystem in fluid communication with the one or more on-board storage tanks;
   a radio frequency subsystem including a microwave generator and a plurality of pyramidal horn antennas, wherein the orientation of the antennas is adjustable; and
   a control system, wherein the one or more on-board tanks, the sprayer subsystem, the radio frequency subsystem, and the control system are housed in the mobile cart;
   spraying the DEE formulation on to the contaminated surfaces disposed external to the mobile cart using the sprayer subsystem to substantially coat the contaminated surfaces to form coated surfaces;
   waiting for a predetermined hold time; and
   generating reactive oxidative species by decomposing the DEE formulation using microwave radiation directed from the microwave generator using the pyramidal horn antennas to the coated surfaces for a predetermined exposure time to substantially decontaminate the coated surfaces to yield treated surfaces.

2. The method of claim 1, wherein the DEE formulation includes about 2.5 wt % percarbonate based stain remover (PCSR) in water.

3. The method of claim 2, wherein the DEE formulation further includes about 1 wt % surfactant in water.

4. The method of claim 1, further including moving the mobile cart using a mobility subsystem including an undercarriage for the mobile cart having wheels powered by a motor, and using input from one or more of computer vision, GPS, ultrasonic proximity sensors, optical sensors, sonar sensors, gyroscopes, or a robotic platform control system disposed in communication with the control system.

5. The method of claim 4, further including remotely controlling the treating of the contaminated surfaces using a human operator.

6. The method of claim 4, further including autonomously controlling the treating of the contaminated surfaces.

7. The method of claim 1, further implementing one or more of the following operations using the control system:
   controlling a power supply;
   spraying a predetermined dosage of DEE formulation from the one or more on-board storage tanks to a plurality of nozzles included in the sprayer subsystem; or
   focusing the microwave radiation onto the coated surfaces by adjusting the orientation of the one or more pyramidal horn antennas.

8. The method of claim 7, further including electrically connecting the power supply with one or more of a battery pack disposed on-board the mobile cart, power supplies available within an aircraft, or power supplies available at ground support when an aircraft is parked at an airport.

9. The system of claim 1, further including measuring the amount of DEE formulation remaining in the one or more on-board storage tanks using one or more of an initial amount of DEE formulation in the one or more on-board storage tanks, a spray rate of the DEE formulation from the one or more nozzles, or spraying time corresponding to the spray rate.

10. The method of claim 1, further including transferring data associated with the treating of contaminated surfaces to a remote server using one or more of data acquisition components and data transfer components disposed in the mobile cart, and in communication with the control system, wherein the data includes one or more of:

a composition of DEE formulation;

an amount of DEE formulation used for treating contaminated surfaces;

an amount of DEE formulation remaining in the one or more on-board storage tanks;

frequency of microwave radiation;

the predetermined hold time;

microwave radiation predetermined exposure time; or a type of surface contaminant disposed on the contaminated surfaces.

11. The method of claim 1, wherein the treated surfaces are characterized by a surface contaminant reduction of at least 6-log reduction.

12. The method of claim 1, wherein the predetermined hold time is between about 15 s and about 45 s.

13. The method of claim 1, wherein the contaminated surfaces include one or more of surfaces inside hospital rooms, aircrafts, or office buildings.

14. The method of claim 1, wherein the contaminated surfaces include surface contaminants including one or more of 229E (alpha coronavirus), NL63 (alpha coronavirus), OC43 (beta coronavirus), HKU1 (beta coronavirus), MERS-CoV, SARS-CoV, or SARS-Coronavirus-2.

15. The method of claim 1, wherein the microwave radiation is characterized by a frequency of between about 2.35 GHz and about 2.65 GHz.

16. The method of claim 1, wherein the microwave radiation is characterized by a frequency of about 2.45 GHz.

17. The method of claim 1, wherein the microwave radiation is characterized by heat output of between about 500 W about 2000 W.

18. The method of claim 1, wherein the predetermined exposure time is between about 10 s and about 45 s.

19. The method of claim 1, wherein the predetermined exposure time is between about 15 s and about 30 s.

* * * * *